(12) United States Patent
Loewe et al.

(10) Patent No.: US 11,198,099 B2
(45) Date of Patent: Dec. 14, 2021

(54) POROUS TEXTILE FABRIC, FILTER ELEMENT, METHOD FOR THE PRODUCTION THEREOF AND USE THEREOF

(71) Applicant: Sartorius Stedim Biotech GmbH, Göttingen (DE)

(72) Inventors: Thomas Loewe, Göttingen (DE); Thomas Friese, Bleicherode (DE); Sebastian Handt, Göttingen (DE); Mario Strauss, Bad Lauterberg (DE); Paschalis Nikoloudis, Göttingen (DE)

(73) Assignee: Sartorius Stedim Biotech GmbH

( * ) Notice: Subject to any disclaimer, the term of this patent is extended or adjusted under 35 U.S.C. 154(b) by 301 days.

(21) Appl. No.: 16/346,088

(22) PCT Filed: Oct. 30, 2017

(86) PCT No.: PCT/EP2017/001267
§ 371 (c)(1),
(2) Date: Apr. 29, 2019

(87) PCT Pub. No.: WO2018/077476
PCT Pub. Date: May 3, 2018

(65) Prior Publication Data
US 2020/0055002 A1    Feb. 20, 2020

(30) Foreign Application Priority Data

Oct. 31, 2016  (DE) ..................... 10 2016 013 019.9

(51) Int. Cl.
*B01D 53/22*   (2006.01)
*B01D 69/12*   (2006.01)
(Continued)

(52) U.S. Cl.
CPC ............. *B01D 69/12* (2013.01); *A61L 9/16* (2013.01); *B01D 46/543* (2013.01);
(Continued)

(58) Field of Classification Search
CPC .. B01D 69/12; B01D 2271/025; B01D 69/02; B01D 46/543; B01D 65/003;
(Continued)

(56) References Cited

U.S. PATENT DOCUMENTS 3,427,394 A * 2/1969 Mckean ............... H01B 7/0225
174/36
5,643,240 A * 7/1997 Jackson ............ A61F 13/51121
604/378
(Continued)

FOREIGN PATENT DOCUMENTS

| DE | 4234816  | 10/1993 |
|----|----------|---------|
| DE | 19543955 | 5/1997  |

(Continued)

OTHER PUBLICATIONS

International Search Report and Written Opinion for PCT/EP2017/001267, dated Jan. 16, 2018.

*Primary Examiner* — Anthony R Shumate
(74) *Attorney, Agent, or Firm* — Klarquist Sparkman, LLP (57) ABSTRACT

The present invention relates to a porous sheet product, to a filter element comprising the porous sheet product, to a method for producing the porous sheet product, to a method for producing the filter element, and to the use of the sheet product and of the filter element.

8 Claims, 5 Drawing Sheets

(51) Int. Cl.
  *A61L 9/16* (2006.01)
  *B01D 46/54* (2006.01)
  *B01D 65/00* (2006.01)
  *B01D 65/02* (2006.01)
  *B01D 69/02* (2006.01)
  *B01D 71/26* (2006.01)
  *B01D 71/48* (2006.01)

(52) U.S. Cl.
  CPC ......... *B01D 65/003* (2013.01); *B01D 65/022* (2013.01); *B01D 69/02* (2013.01); *B01D 71/26* (2013.01); *B01D 71/48* (2013.01); *A61L 2209/14* (2013.01); *A61L 2209/22* (2013.01); *B01D 2271/025* (2013.01); *B01D 2279/65* (2013.01); *B01D 2325/28* (2013.01); *B01D 2325/38* (2013.01)

(58) Field of Classification Search
  CPC ...... B01D 65/022; B01D 71/26; B01D 71/48; B01D 2279/65; B01D 2325/28; B01D 2325/38; A61L 9/16; A61L 2209/14; A61L 2209/22
  See application file for complete search history.

(56) References Cited

U.S. PATENT DOCUMENTS

| | | | | |
|---|---|---|---|---|
| 6,186,341 B1* | 2/2001 | Konstantin | .......... | B01D 63/061 210/488 |
| 6,977,111 B2* | 12/2005 | Yamaguchi | ............. | B32B 29/00 427/256 |
| 2007/0125700 A1* | 6/2007 | Ding | .................. | B01D 39/2041 210/490 |
| 2007/0125703 A1* | 6/2007 | Chapman | ............. | B01D 39/086 210/504 |
| 2008/0113172 A1* | 5/2008 | Acosta | .................. | C07C 271/22 428/220 |
| 2008/0113573 A1* | 5/2008 | Acosta | ................ | D06M 13/513 442/76 |
| 2009/0047435 A1* | 2/2009 | Hutchenson | .......... | C07C 275/28 427/384 |
| 2009/0047498 A1* | 2/2009 | Hutchenson | ...... | C07C 273/1827 428/304.4 |
| 2015/0013295 A1* | 1/2015 | Uchiyama | .............. | D04H 1/541 55/524 |
| 2019/0329172 A1* | 10/2019 | Wunn | ..................... | B32B 5/024 |
| 2020/0055002 A1* | 2/2020 | Loewe | .................. | B01D 69/12 |

FOREIGN PATENT DOCUMENTS

| | | |
|---|---|---|
| DE | 19729456 | 10/1998 |
| DE | 102010056148 | 1/2013 |
| DE | 102011121018 | 6/2013 |
| JP | 2002058974 | 2/2002 |
| JP | 2006289174 | 10/2006 |
| WO | WO97/19743 | 6/1997 |
| WO | WO00/04984 | 2/2000 |
| WO | WO2012/031653 | 3/2012 |

* cited by examiner

Figure 5

POROUS TEXTILE FABRIC, FILTER ELEMENT, METHOD FOR THE PRODUCTION THEREOF AND USE THEREOF

CROSS REFERENCE TO RELATED APPLICATIONS

This is the U.S. National Stage of International Application No. PCT/EP2017/001267, filed Oct. 30, 2017, which in turn claims the benefit of German Application No. 102016013019.9, filed Oct. 31, 2016, which application is incorporated herein in its entirety.

FIELD

The present invention relates to a porous sheet product, to a filter element comprising the porous sheet product, to a method for producing the porous sheet product, to a method for producing the filter element, and to the use of the sheet product and of the filter element.

SUMMARY

Disclosed in the prior art are filter elements comprising a porous sheet product, which comprises porous membrane plies and porous separation or reinforcement plies, and also one or more anchoring elements, the sheet product being embedding therein. For example, the sheet products are pleated in a tubular or astral manner. The two ends of the sheet products are embedded into end caps, which act as anchoring elements. The embedding is usually done by immersion of the edge regions of the sheet product into the melted anchor. According to the prior art, the porous separation plies are polyester spunbonded nonwovens, for example polyethylene terephthalate spunbonded nonwovens, hereinafter referred to as PET spunbonded nonwovens, which can be used to build gamma-sterilizable pleated filter elements. Polyester spunbonded nonwovens are gamma-stable up to a radiation dose of approx. 1000 kGy. The porous membrane plies of such filter elements are intended to be sterilizable by gamma-radiation.

Figure 1:
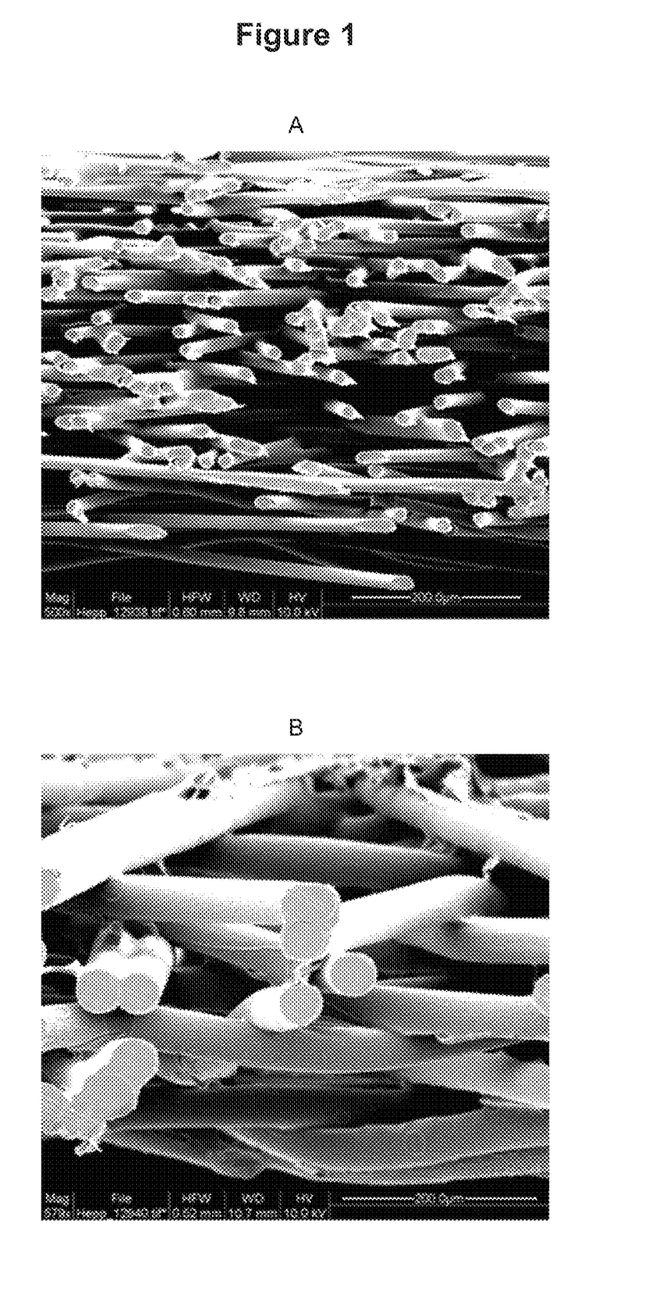
FIG. 1 shows SEM images ("SEM" stands for scanning electron microscopy) of, in each case, a porous separation ply B of an exemplary sheet product according to the present invention.
Figure 2:
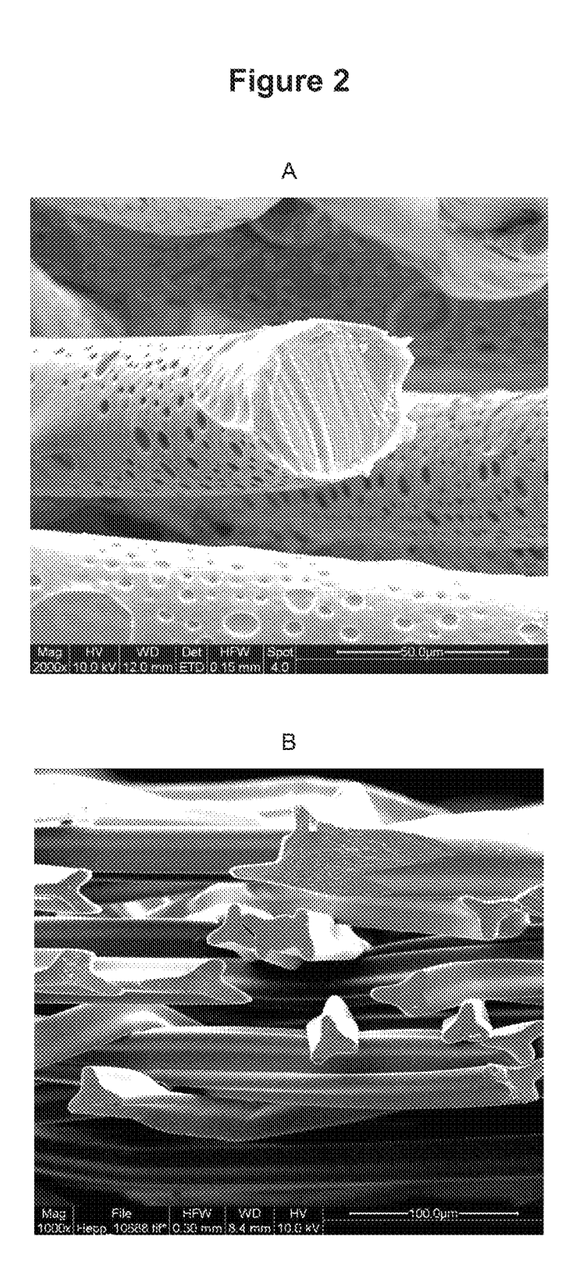
FIG. 2 shows SEM images of a PP/PE core-sheath spunbonded nonwoven at 2000-fold magnification (A) and of a PET spunbonded nonwoven at 1000-fold magnification (B), the nonwovens from FIGS. 2A and 2B exhibiting the same drainage action.
Figure 3:
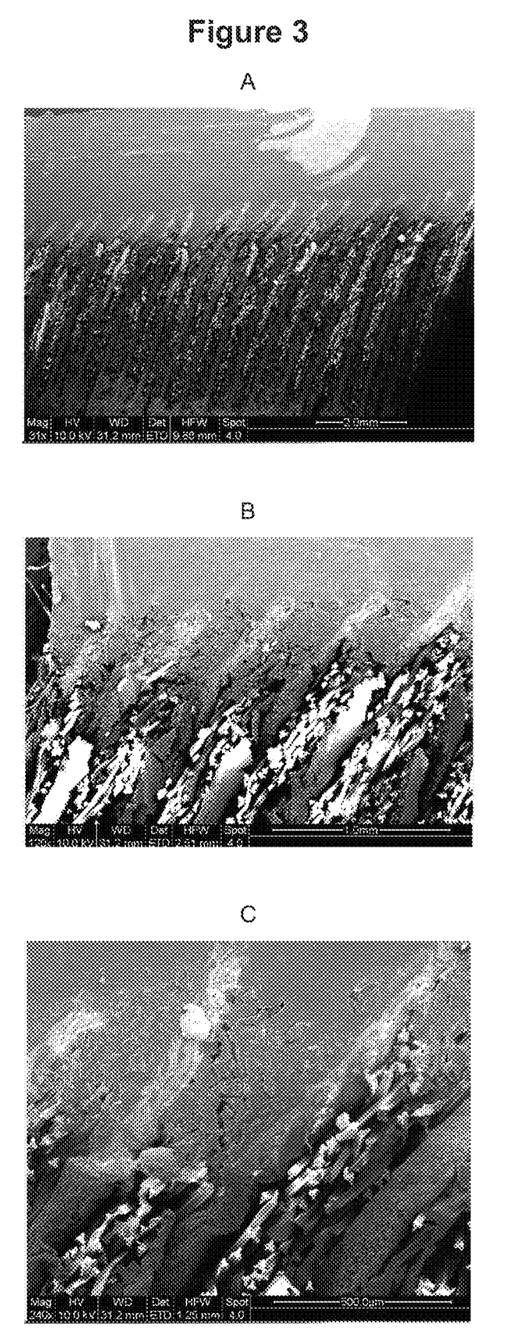
FIG. 3 shows, in different magnifications, SEM images of a cap section (section through the end caps of the filter element) of a filter element according to the prior art, using a polyester nonwoven instead of a porous separation ply composed of polyolefin core-sheath fibers. Especially in the magnifications B and C, it can be clearly seen that the polyester fibers have not completely melted in the embedding region and that the polyester nonwoven has hardly shrunk back, resulting in bypasses being allowed to form.
Figure 4:
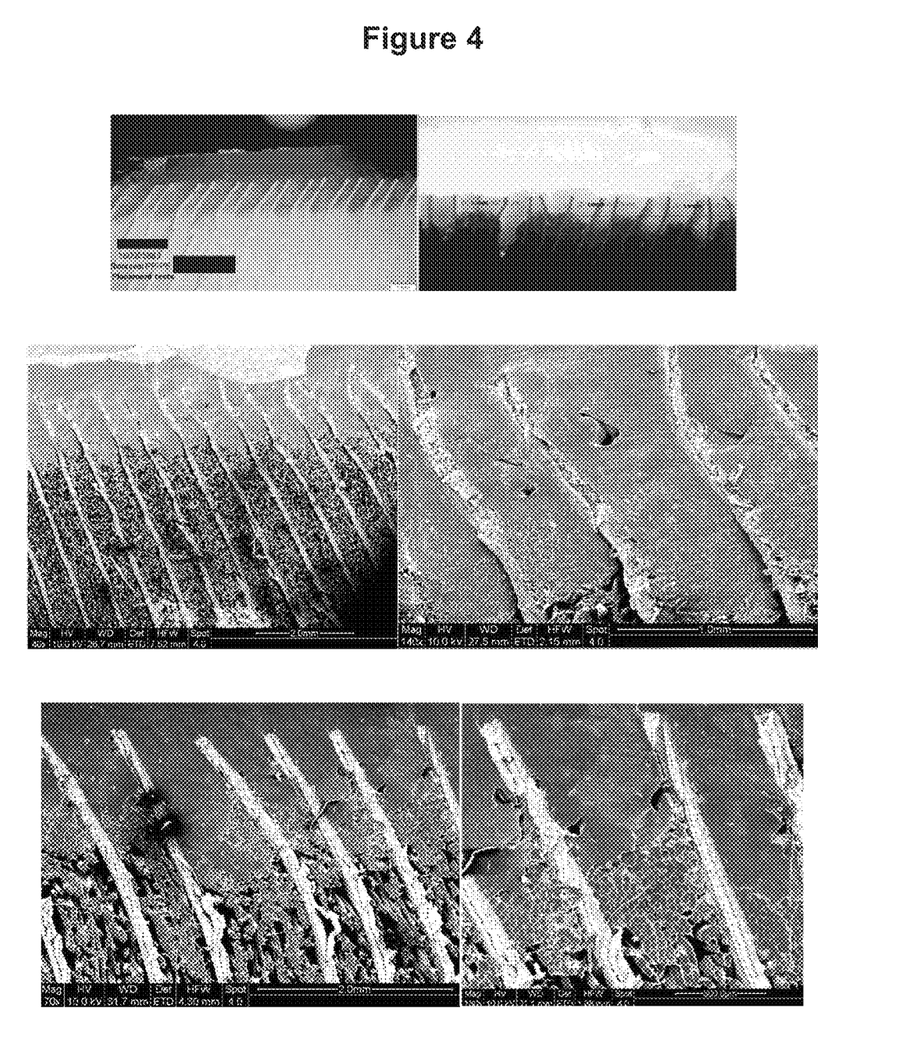

However, the high melting point of the PET spunbonded nonwovens of about 250° C. has a disadvantageous effect on the end product to be manufactured, on the processing in the construction of filter elements to form sterile membrane filters. For instance, what may possibly occur (owing inter alia to the thickness of the individual PET fibers) is the formation of liquid-tightness defects or bypasses in the region of embedding. When the edge regions of the sheet product are immersed into the melted anchor, nonmelting PET fibers lead to an incomplete seal (see FIG. 3). This defect takes effect to a particularly great extent when constructing single-ply membrane filter elements, since they exhibit a lower mechanical stability in comparison with two-ply membrane filter elements and therefore cannot be exposed to excessive forces during embedding into the melted anchor.

Using the conventional porous separation plies with high melting temperature, it is not possible to achieve an increased mechanical stability by increasing the fiber thickness and/or the thickness of the separation plies. Since the conventional separation plies only melt at a relatively high temperature, a satisfactory connection to the anchoring elements of a filter element cannot be achieved in the case of high thicknesses of the fibers and/or the separation plies owing to insufficient separation-ply melting. The occurrence of liquid-tightness defects/bypasses would be enhanced even more as a result.

It is an object of the present invention to provide a radiation-resistant porous sheet product which is intended to allow the production of filter elements with anchoring elements without the formation of bypasses, to provide a corresponding filter element and to provide methods for producing the sheet product and the filter element.

This object is achieved by the embodiments characterized in the claims.

BRIEF DESCRIPTION OF THE DRAWINGS

FIG. 4 shows different images of a cap section of a filter element according to the present invention. It can be clearly seen that the porous separation plies B have shrunk back and that the membrane plies A are completely encased in the region of embedding and intimately meshed with the anchoring element, resulting in the avoidance of the formation of bypasses.

DETAILED DESCRIPTION

In one aspect, the present invention provides a porous sheet product having at least one of the following ply A and at least one of the following ply B:
  A: a porous membrane; and
  B: a porous separation or reinforcement ply constructed from polyolefin core-sheath fibers, the sheath material having a lower melting temperature than the core material;
  the porous sheet product exhibiting a radiation resistance of at least 20 kGy.

According to the invention, the porous separation ply B is constructed from polyolefin core-sheath fibers. Preferably, the porous separation ply B consists of polyolefin core-sheath fibers. Particularly preferably, the sheath material is polyethylene. Polyethylene is distinguished by a high radiation resistance, and this makes a positive contribution to the radiation resistance of the sheet product according to the invention. Moreover, polyethylene has a relatively low melting point. In the production of a filter element, this can ensure that, when anchoring the sheet product according to the invention in an anchoring element, the sheath material completely melts in the region of the anchoring element. It was found that, surprisingly, the separation ply B shrinks back as a result of melting of the sheath material of the core-sheath fibers, with the result that, in the region of the anchoring element, the membrane ply A protrudes further than the separation ply B into the at least partially melted material of the anchoring element. This leads to a firm embedding and, in the case of multiple membrane plies A, even to an intimate meshing between the anchoring element material and the sheet product according to the invention, resulting in the avoidance of bypasses in the region of the anchoring element of the filter element. The avoidance of bypasses is essential especially when producing sterile filters. The core material of the core-sheath fibers exhibits a higher melting temperature than the sheath material. As a result, it is possible to melt the sheath material without altering the structure of the porous separation ply (apart from the desired shrinkage effect).

Furthermore, the specific structure of the sheet product according to the invention makes it possible to pleat the sheet product gently, i.e., at a low temperature, and this is advantageous especially in the case of a hydrophobically modified membrane ply A, which may be heat-sensitive.

Preferably, the difference between the melting temperatures of the sheath and core materials is at least 5° C., particularly preferably at least 15° C. and especially preferably at least 25° C. The difference is, for example, not greater than 100° C., preferably 75° C., and especially preferably not greater than 50° C.

Preferably, the core material is polypropylene (PP), having a melting point within the range of 150° C.±10° C. for example. The sheath material is preferably polyethylene (PE), having a melting point within the range of 135° C.±5° C., 120° C.±5° C. or 105° C.±5° C. for example. Preferably, the sheath material consists of at least one of LDPE (low-density polyethylene) and HDPE (high-density polyethylene) or a mixture thereof, and particular preference is given to HDPE.

It is further preferred that the core material is polypropylene (PP) having a melting point within the range of 160° C.±10° C. and/or that the sheath material is polyethylene (PE) having a melting point within the range of 112.5° C.±10° C. Particular preference is given to a combination of a core material which is polypropylene (PP) having a melting point within the range of 160° C.±5° C., especially preferably 160° C.±2° C., and of a sheath material which is polyethylene (PE) having a melting point within the range of 112.5° C.±5° C., especially preferably 112.5° C.±2° C. and most preferably 112.5° C.±1° C.

According to the invention, the melting point can be measured using a calorimeter with differential scanning. Suitable therefor is, for example, the calorimeter model "DSC 214 Polyma" from Netsch.

The mass ratio of the polymers PP:PE (core polymer: sheath polymer) in the core-sheath fibers can vary between 2:98 to 90:10, with preference being given to a ratio of from 30:70 to 70:30, especially 40:60 to 60:40, for example 50:50.

According to a preferred embodiment of the present invention, the core-sheath fibers exhibit an approximately circular cross-sectional profile. Particularly preferably, the core fibers also exhibit an approximately circular cross-sectional profile.

"Diameter" is understood according to the invention to mean the greatest longitudinal dimension in the cross-sectional profile.

According to the invention, the diameter of the core-sheath fibers is preferably 10 to 200 µm, particularly preferably 25 to 100 µm and especially preferably 30 to 50 µm. It should be noted here that, in the case of a large diameter of the core-sheath fibers, for example 25 to 200 µm, preferably 30 to 200 µm, particularly preferably 50 to 200 µm and especially preferably 75 to 200 µm, it is possible according to the invention to provide a porous separation ply B having high porosity and low flow or air resistance. Therefore, a large diameter of the core-sheath fibers makes it possible to reduce the flow resistance of the porous separation ply B, and this makes a corresponding sheet product according to the invention particularly suitable for air filtration.

The diameter of the core fibers without sheath is preferably 1 to 190 µm, particularly preferably 2 to 100 µm and especially preferably 5 to 45 µm.

The thickness of the sheath is preferably 1 to 150 µm, preferably 2 to 75 µm, especially preferably 5 to 15 µm. "Thickness of the sheath" is understood to mean the greatest longitudinal dimension measured from the interface between core and sheath up to the external surface of the core-sheath fibers and perpendicular to the interface between core and sheath.

Preferably, the separation ply B exhibits a shrinkage after autoclaving at a temperature of 121° C. for a period of 30 minutes of at least 2%, preferably at least 4% and especially preferably at least 5%. The shrinkage is calculated according to the following equation:

$$\text{Shrinkage}[\%]=100\%\cdot(1-(\text{length of separation ply B after autoclaving}/\text{length of separation ply B before autoclaving})$$

Furthermore, the separation ply B preferably exhibits a shrinkage due to heating to 130° C. (which is different from shrinkage due to autoclaving) of not more than 1.5%, preferably not more than 1.0%. Furthermore, it is preferred that the separation ply B exhibits a shrinkage due to heating to 140° C. (which is different from shrinkage due to autoclaving) of not more than 2.5%, preferably not more than 2%. The above values can be minimized especially when the separation ply B is constructed from a polyolefin material (e.g., polyethylene-polypropylene core-sheath fibers).

The shrinkage due to heating to 130° C. or the shrinkage due to heating to 140° C. can be determined as follows.

Shrinkage due to heating to 130° C. or shrinkage due to heating to 140° C.

A circular punched blank (diameter 142 mm) is placed onto a hot plate having a temperature of 130° C. or 140° C. for 10 seconds. The percentage reduction in the diameter, based on the original diameter of the punched blank, is used as shrinkage due to heating.

According to a further preferred embodiment of the present invention, the sheet product is pleated. Particularly preferably, the sheet product is pleated with the folds having different fold heights, as described for example in DE 102010056148 B4.

Owing to the specific properties of the porous separation ply, the sheet product according to the invention exhibits an excellent thermoplastic deformability. As a result, it is possible by application of heat and mechanical force to achieve a stable pleating composite which is difficult to deform perpendicular to the pleating (no "accordion effect"). Moreover, the high stability facilitates the anchoring of the pleated sheet product (which can also be referred to as "plissé ") in an anchoring element in the method according to the invention for producing a filter element.

The arrangement of the plies A and B is not subject to any particular restriction. Sheet products according to the invention can exhibit a solely alternating ply sequence (ABA-BAB, etc.), or can exhibit ply sequences in which two or more identical plies follow one another (e.g., AAB or BBA). Preferably, in the sheet product according to the invention, adjacent plies are directly adjacent. This means that no further plies are inserted between adjacent plies and that adjacent plies lie against one another. Moreover, it is preferred that the two external plies of the sheet product are formed by one ply B in each case. Particularly preferably, the sheet product according to the invention consists of alternating plies having two plies B as outermost plies, i.e., the ply sequence is B(AB)n, where n is an integer.

According to a preferred embodiment of the present invention, the sheet product consists of the ply sequence BAB, i.e., n=1 in the above preferred ply sequence B(AB)n. Such a sheet product is referred to as "single-ply", this designation being determined by the number of membrane plies A. Thus, for example, a sheet product having two membrane plies A is referred to as two-ply. The single-ply sheet product according to the invention composed of the ply sequence BAB is particularly suitable for the filtration of solutions and gases. The sheet product is particularly suitable for the filtration of solutions containing solvents which wet hydrophobic membranes, for example nonpolar solvents. The single-ply sheet product is especially suitable for the sterile-filtration of air.

According to a further preferred embodiment, the porous sheet product according to the invention comprises two successive membrane plies A. Particularly preferably, the two membrane plies are two different porous membranes $A_1$ and $A_2$, for example a preliminary filter and a main filter. For example, $A_1$ and $A_2$ differ in their pore size. Particularly preferably, the sheet product consists of the ply sequence B(AAB)n, where n is an integer and preferably 1.

According to the present invention, the plies A and B can lie on top of one another in a loose manner without being firmly connected to one another. However, it has been found to be advantageous to fix the porous separation ply B and the membrane ply A by means of a physical and/or chemical connection between directly adjacent plies. The physical and/or chemical connection can, for example, be effected by a lamination process using known devices, or by pressure and temperature action during the further processing of the sheet product according to the invention, for example to form a plissé. Preferably, the membrane ply A is laminated onto the ply B, as disclosed for example in DE-C1 42 34 816. The lamination is preferably effected only in a punctiform manner, resulting in the obtaining of a sufficient connection between the plies A and B and simultaneously a sheet product with high flow capacity. Such lamination can, for example, be achieved by pleating with a pleating temperature below the melting temperature of the porous sheet product and with application of a pleating contact pressure. In particular, preference is given to laminating the membrane ply A with the porous membrane ply B only in the edge region of the sheet product because, in this case, a sheet product with very high flow capacity can be obtained.

To achieve a highest possible flow capacity, it is preferred that the plies A and B lie on top of one another in a loose manner without being firmly connected to one another. In other words, only loose contact can exist between the plies A and B without the plies being firmly connected to one another. A physical/chemical connection (e.g., due to lamination) may close the surface pores of the membrane, the result being that the filter properties may deteriorate. Furthermore, the generation of such a connection is associated with considerable effort. Furthermore, the further processing (e.g., pleating/folding) of a laminated sheet product may lead to defects in the membrane ply A. For example, it is possible that, in the case of a laminated sheet product, fiber ends of the separation ply B penetrate into the membrane ply A and defects in the form of pinholes are generated as a result. Therefore, it is advantageous, especially with respect to filtration capacity, for A and B to lie on top of one another in a loose manner.

The sheet product according to the invention exhibits a radiation resistance of at least 20 kGy, preferably at least 50 kGy and particularly preferably at least 100 kGy. The radiation resistance of the sheet product according to the invention does not have an upper limit and is preferably not more than 500 kGy, particularly preferably not more than 200 kGy. According to the invention, a "radiation resistance of X kGy" is understood to mean that the loss of strength of the sheet product after gamma-irradiation with a dose of X kGy is not more than 30% (X can assume any value and is, for example, 20 kGy, 50 kGy, 100 kGy or 500 kGy). The loss of strength arises in this connection from the decrease in the strength value of the sheet product after the gamma-irradiation with a dose of X kGy, based on the strength value of the sheet product before the gamma-irradiation with said dose. If the strength value of the irradiated sheet product is 80% of the strength value of the unirradiated sheet product, the loss of strength is 20% according to the invention. In the context of the present invention, the strength values of the irradiated and unirradiated sheet products are described by their maximum tensile force values $F_{max}$ at room temperature. To determine $F_{max}$, a sample of the sheet product measuring 20 mm×150 mm is cut out for this purpose and clamped horizontally into a "Zwick Z2.5/TN1S" material-testing machine from Zwick GmbH such that the free sample length between the clamping jaws is 4 cm. The force transducer "KAP-Z 200N" (A.S.T., 01287 Dresden, Germany) is moved at a speed of, for example, 5 cm/min. The measurement data are continuously captured and visualized by the instrument software "testXpert" (Zwick GmbH, 89079 Ulm, Germany). $F_{max}$ is determined as the mean of three irradiated samples of the sheet product or three unirradiated samples. Owing to the radiation resistance of the sheet product according to the invention, the sheet product, or the filter element according to the invention formed therefrom, does not have to autoclaved for the purpose of sterilization, but can instead be antimicrobially prepared for use by high-energy radiation, for example gamma-radiation. Consequently, the sheet product according to the invention and the filter element according to the invention are, owing to the radiation resistance of the sheet product, particularly suitable for the sterile-filtration of gaseous fluids and, in particular, for the sterile-filtration of air.

According to a preferred embodiment of the present invention, the porous separation ply B is a nonwoven, woven, knitted fabric and/or lattice, with preference being given to a nonwoven, especially a spunbonded nonwoven. This embodiment can ensure a particularly high dimensional stability of the porous separation ply B.

According to a preferred embodiment of the present invention, the porous separation ply B exhibits a thickness of at least 200 μm, particularly preferably of at least 300 μm and especially preferably of at least 350 μm. Owing to thicknesses within this range, it is possible to provide a sheet product according to the invention having high mechanical strength and high rigidity. A high rigidity of the sheet product is advantageous especially for the production of the filter element according to the invention, especially when using single-ply sheet products having only one membrane ply A. It should be taken into account here that a larger diameter of the core-sheath fibers should be associated with a larger thickness of the porous separation ply.

The upper limit of the thickness is not subject to any particular restriction, though a thickness of not more than 700 µm, preferably 600 µm, should not be exceeded.

According to a preferred embodiment of the present invention, the porous separation ply B exhibits, at a pressure of $1.25 \cdot 10^2$ Pa, a mean air permeability of from 1500 to 4000 $dm^3/m^2s$, preferably 2600 to 3000 $dm^3/m^2s$ and particularly preferably 1800 to 2500 $dm^3/m^2s$. Mean air permeability can be determined as described as follows.

Determination of Mean Air Permeability

Taken as a basis are 10 different punched test blanks of a material to be investigated (e.g., a nonwoven). The air permeability of each of the punched test blanks having an area of 20 $cm^2$ each is measured using the air-permeability tester model "FX 3300 LABOTESTER III" from TEXTEST INSTRUMENTS. In each of the 10 measurements, the differential pressure is 125 Pa. The measurement yields 10 values (unit: $1/m^2/min$). The mean air permeability is the arithmetic mean from said 10 values.

A person skilled in the art is capable of setting the air permeability of the porous separation ply B on the basis of his/her knowledge.

The porous separation ply B preferably exhibits a mean flow pore size of at least 100 µm, further preferably at least 110 µm, particularly preferably at least 120 µm, especially preferably at least 130 µm and even more preferably at least 140 µm. This ensures that the porous separation ply B exhibits a sufficient air permeability. The porous separation ply B preferably exhibits a mean flow pore size of not more than 600 µm, further preferably not more than 500 µm. This ensures that the separation ply B exhibits a sufficient stability.

Mean flow pore size can be determined as described as follows.

Determination of Mean Flow Pore Size

To determine the mean flow pore size, the air flow of a test piece is first determined in the dry state. Thereafter, the test piece is wetted with a liquid and pressure is applied to said test piece via a pressure ramp. Owing to the rise in air pressure, more and more pores are opened successively (from large to small). By means of the correlation of pressure and air flow, it is possible to assign various pore sizes to certain pressure values. The mean flow pore size is the pore size (or the pressure assignable thereto), wherein the air flow is half the air flow of the dry test piece.

The measurement is carried out using the porometer model "Porolux 500" from IB-FT GmbH. To this end, a circular sample is punched out (18.5 mm diameter), wetted with perfluoropolyether, loaded into the porometer and measured (shape factor: 0.715; initial pressure and final pressure: 0 and 0.02 bar, respectively; number of steps: 20; time/pressure increase: 2000 s/bar). Calculation of first bubble point was done on the basis of the first-flow method. The arithmetic mean from three measurements is used as the mean pore flow size.

In a further preferred embodiment, the porous separation ply exhibits a basis weight of from 85 to 120 $g/m^2$, preferably 95 to 110 $g/m^2$.

Preferably, the ply A is a hydrophobic porous membrane. In this context, "hydrophobic" means that the surface tension of the material which forms the surface of the membrane exhibits a contact angle of more than 90° with respect to water. The contact angle can, for example, be measured in accordance with ISO15989.

In many cases, synthetic polymers have hydrophobic surface properties which can be attributed to the intrinsic hydrophobicity of the synthetic materials. Hydrophobicity is a material constant. It is caused by the extramolecular interactions of the atomic groups forming the basis of the polymer.

Owing to their low surface tension with respect to water, these materials exhibit a reduced wettability with aqueous and polar media. For smooth, nonporous surfaces, the contact angle with respect to water is a measure of the surface tension. Surfaces having a contact angle of more than 90° with respect to water are referred to as hydrophobic. Hydrophobic substances are not miscible or wettable with water. The substances are usually nonpolar, and their surface tension is below 72 mN/m at 20° C. Oleophobic substances, which are distinguished by a particularly high hydrophobicity, are not miscible or wettable with oils and other nonpolar substances. Their surface tension is less than 21 mN/m at 20° C. Typical surface tensions of polymers which are processed to form membranes, and the contact angle thereof with respect to water, are listed in Table 1.

TABLE 1

Surface tensions of smooth, nonporous polymers and the contact angle thereof with respect to water

| Polymer | Surface tension [mN/m] | Contact angle with respect to water [°] |
|---|---|---|
| Polyamide (nylon) | 75[a] | 49[a] |
| Polyethersulfone (PES) | 58[a] | 54[a] |
| Polyether ether ketone (PEEK) | 49[a] | 71[a] |
| Polyethylene (PE) | 31[b] | 94[b] |
| Polyvinylidene fluoride (PVDF) | 25[b] | 85[b] |
| Polytetrafluoroethylene (PTFE) | 18.5[b] | 108[b] |

[a]Membrane Science and Technology Series, 11, "Membrane Contactors: Fundamentals, Applications and Potentialities", 2005, E. Drioli et al.
[b]J. Appl. Polym. Sci., 1969, 13, 1741-1747, D. K. Owens et al.

According to a preferred embodiment of the present invention, the hydrophobic porous membrane ply A is intrinsically hydrophobic and/or hydrophobically modified, the hydrophobic porous membrane ply A being particularly preferably hydrophobically modified.

According to the invention, an intrinsically hydrophobic porous membrane ply A is constructed from a hydrophobic material. According to a preferred embodiment of the present invention, the porous membrane is constructed from a polymer selected from the group consisting of polyethersulfone, polyvinylidene fluoride and polyolefins (e.g., polyethylene) and also mixtures thereof. Particularly preferably, the porous membrane is constructed from polyethersulfone.

According to the present invention, a hydrophobic modification can be effected using fluorine-containing agents, for example in monomeric, oligomeric or polymeric form. Suitable modification methods are known to a person skilled in the art. For example, the membrane described in DE 10 2011 121 018 A1 can be used as hydrophobically modified membrane.

The porous membrane is preferably constructed from a material, the melting point of which is at least 10° C., preferably at least 25° C. and particularly preferably at least 50° C. higher than the melting point of the sheath material. This can safeguard the structural integrity of the membrane ply A when producing the filter element according to the invention.

According to a preferred embodiment, the porous membrane exhibits a mean pore size of from 0.005 to 10 µm, preferably 0.1 to 1.2 µm and further preferably 0.2 to 0.65 µm.

A classification of porous membranes can be done on the basis of their pore sizes. For instance, on the basis of pore size, a distinction is generally made between microfiltration membranes (mean pore size: 0.1 to 10 µm), ultrafiltration membranes (mean pore size: 0.01 to less than 0.1 µm), nanofiltration membranes (mean pore size: 0.001 to less than 0.01 µm) and reverse-osmosis membranes (mean pore size: 0.0001 to less than 0.001 µm) (see Shang-Tian Yang, Bioprocessing for Value-Added Products from Renewable Resources, 2007).

Mean pore size is, for example, determined as described below.

Method for Determining Mean Pore Size

Different methods are used depending on the pore size to be determined. In the area of microfiltration, capillary flow porometry is primarily used. Capillary flow porometry is a gas/liquid porosimetry in which the differential gas pressures and flow rates across a membrane sample are measured first in the wet state and then in the dry state.

Before the measurement, the membrane sample is contacted with wetting liquid such that all pores present are filled with said liquid. After the filling of the pores and the introduction of the sample, the measurement cell must be closed and the measurement must be started. After the start of the measurement, the gas pressure is increased automatically and in steps, and the pore diameters corresponding to the acting pressure are emptied by the gas pressure. This is carried out until the relevant pore range has been captured, i.e., until even the smallest pores present in the measurement range are cleared of liquid. Thereafter, the pressure is lowered and the measurement is automatically repeated on the now dry sample. From the difference between the two pressure-flow rate curves, the pore size distribution is calculated via the Young-Laplace equation. (See Shrestha, Aabhash, "Characterization of porous membranes via porometry" (2012), Mechanical Engineering Graduate Theses & Dissertations, Paper 38.)

The characterization of the pore size distribution for ultrafiltration and nanofiltration membranes cannot be done by means of a gas/liquid porosimetry, since the pores in said membranes have a distinctly smaller diameter. According to the Laplace equation, the required pressure for the displacement of the wetting liquid at a given surface tension rises to orders of magnitude of up to 50 to 70 bar. Firstly, such pressures make handling difficult and are in some cases limited by the boundary conditions of the apparatus and, secondly, what can be expected in the case of the pressures exerted on the membrane and the thus resultant forces is a change in structure and, in extreme cases, a loss of structural integrity. The physical properties gained here with regard to the pore size distribution would not correspond to those of an intact membrane. To be able to carry out a characterization nevertheless, what is striven for is a lowering of the surface or interfacial tension of the wetting and displacing media. For this reason, use is made of a liquid-liquid displacement of two nonmiscible liquids. The interfacial tension between these two media is distinctly lower than the surface tension between a gas and a liquid. For the displacement of one liquid by another, the Laplace relationship is applicable in analogy to the gas/liquid porosimetry, and a similar measurement method can be used, with the difference that what are recorded are not gas flow rates, but flow rates of the displacing liquid as a function of the differential pressure increase. (See R. Davila, Characterization of Ultra and Nanofiltration commercial Filters by Liquid-Liquid Displacement Porosimetry, 2013.)

In a further aspect, the present invention provides a method for producing the porous sheet product according to the invention, comprising the steps of (1) providing the at least one porous membrane A;
(2) providing the at least one porous separation ply B;
(3) arranging the at least one porous membrane A and the at least one porous separation ply B to form the porous sheet product.

The above remarks with regard to the sheet product according to the invention apply mutatis mutandis to the method for its production.

According to a preferred embodiment, step (3) is followed by a step (4) of laminating the ply A onto the ply B. Suitable lamination methods are known to a person skilled in the art and disclosed, for example, in DE-C1 42 34 816, as already mentioned above. Step (4) can optionally follow the below-described step (5) or be carried out simultaneously therewith.

Step (3) or step (4) can be followed by a step (5) of pleating the sheet product. Suitable pleating methods are known to a person skilled in the art. Preferably, pleating is carried out at a temperature of from 70° C. to 110° C. Within this low temperature range, the sheet product is treated gently, and this is advantageous especially for hydrophobically modified membrane plies A. As already mentioned above, laminating step (4) can be carried out at the same time as or through the pleating step (5).

In a further aspect, the present invention provides a filter element comprising a porous sheet product according to the invention and at least one anchoring element, the edge regions of the porous membrane A of the sheet product being embedded into the anchoring element in a fluid-tight manner. A fluid-tight embedding can be ensured especially when the edge regions of the sheet product are embedded into the anchoring element. The fluid-tight embedding avoids bypasses in the region of the anchoring elements, as already explained above. As a result, it is possible to provide filter elements according to the invention having excellent filter properties. Because of the fluid-tight anchoring, the filter element is especially suitable for sterile-filtration, in particular for the sterile-filtration of air.

Furthermore, it is preferred that the filter element according to the invention exhibits a BCT value in accordance with ASTM F838-15 of 0 CFU. "CFU" is the acronym for "colony forming units".

According to a preferred embodiment, filter elements having a minimum filter area of 0.15 $m^2$ are WIT-testable ("WIT" stands for "water intrusion test"). The WIT value is dependent on the filter area and the ply sequence. "WIT-testable" means that, for example, a filter element having a single-ply sheet product with the ply sequence BAB, A being a hydrophobically modified polyethersulfone membrane, and a filter area of 0.17 $m^2$ exhibits a WIT value of not more than 5 ml/10 min, preferably not more than 4 ml/10 min and especially preferably not more than 3 ml/10 min, for example 0.3 ml/10 min or less. In the case of a filter area of 0.34 $m^2$ and otherwise identical conditions, "WIT-testable" means that the WIT value is not more than 6.5 ml/10 min, preferably not more than 5.5 ml/10 min, particularly preferably not more than 4.5 ml/10 min and especially preferably not more than 0.45 ml/10 min; in the case of a filter area of 0.53 $m^2$ and otherwise identical conditions, not more than 8 ml/10 min, preferably not more than 7 ml/10 min, particularly preferably not more than 6 ml/10 min and especially preferably not more than 2.6 ml/10 min. The method for WIT value determination is specified in the examples.

The shape of the sheet product, especially in the filter element according to the invention, is not subject to any particular restriction. The sheet product can be present pleated in an astral manner or tubular, as is the case for example for filter capsules, filter cartridges or tubular modules, or else in largely planar form, as is the case for example for disposables.

Preferably, the anchoring element in the region of embedding comprises a thermoplastic polymer material; particularly preferably, the anchoring element consists of a thermoplastic polymer material. As a result, it is possible to achieve a particularly stable and fluid-tight embedding/anchoring by melting of the thermoplastic polymer material in the region of embedding and subsequent placement of the anchoring element onto the sheet product.

According to a preferred embodiment of the present invention, the filter element comprises two anchoring elements, the anchoring elements being end caps of a tubular filter element. It is preferred here that the sheet product is pleated in an astral manner.

According to a further preferred embodiment, the filter element comprises a backflow-buildup safeguard and a core.

According to a preferred embodiment of the present invention, the filter element is an air filter. Insofar as the sheet product according to the invention comprises a hydrophobic membrane ply A and a separation ply B constructed from likewise hydrophobic polyolefin core-sheath fibers, it is particularly suitable for the filtration of air.

In a further aspect, the present invention provides a method for producing the filter element according to the invention, comprising the steps of:

(I) providing a porous sheet product according to the present invention;

(II) providing at least one anchoring element;

(III) embedding the edge regions of the porous membrane A into the at least one anchoring element in a fluid-tight manner.

Suitable fluid-tight embedding methods are known to a person skilled in the art. For example, the anchoring element, if it comprises a thermoplastic polymer material in the region of embedding, can be melted in the region of embedding by heating, followed by a step of placing the anchoring element onto the edge region of the sheet product. Accordingly, according to a preferred embodiment of the present invention, step (III) comprises the steps of (IIIa) melting the thermoplastic polymer material which is comprised by the anchoring element in the region of embedding; and (IIIb) placing the anchoring element onto the edge region of the sheet product.

Step (IIIb) is preferably carried out at a temperature of the melted thermoplastic polymer material of from 180° C. to 600° C., particularly preferably 200° C. to 400° C. and especially preferably 220° C. to 300° C. Temperatures in this low range avoid an excessive action of heat on the sheet product. As a result, undesired changes, especially in membrane ply A, are avoided. Especially in the case of a hydrophobically modified membrane ply A, an excessively high temperature of the thermoplastic material can damage the hydrophobic modification, the result being that the efficiency of the filter element, especially as air filter, may be reduced owing to partial hydrophilization.

The present invention will be more particularly elucidated on the basis of the following nonlimiting examples.

EXAMPLES

Figure 5:
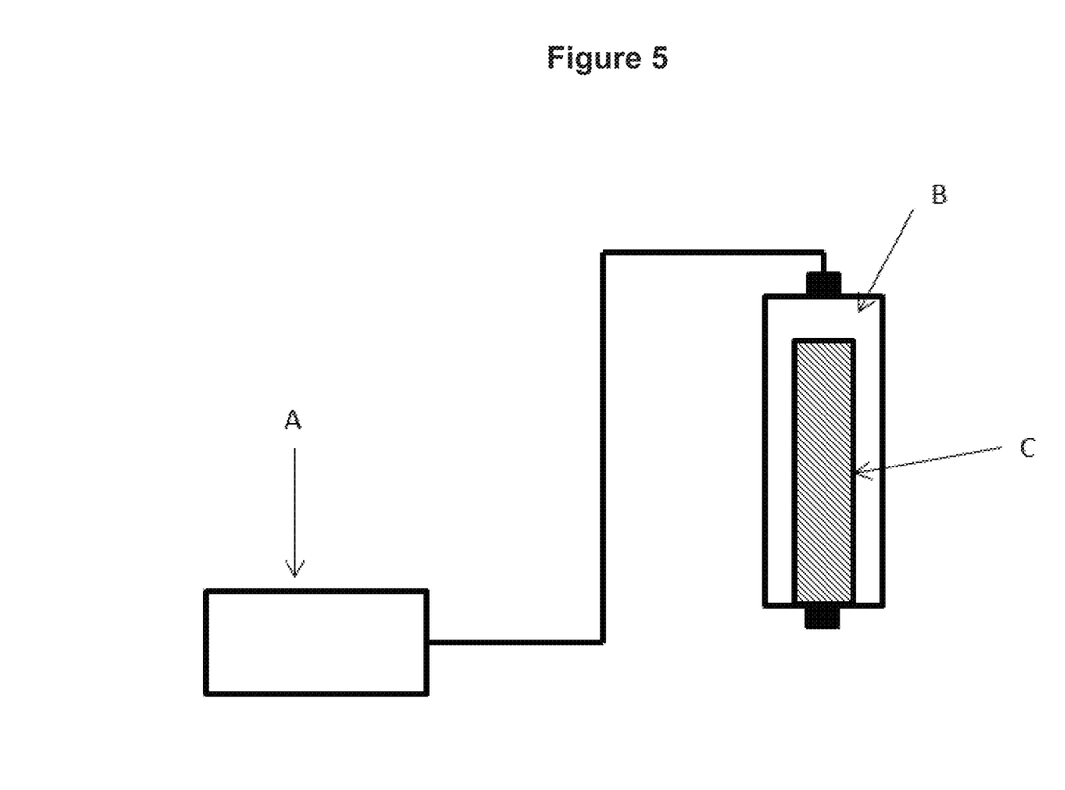
FIG. 5 shows schematically the test setup of Example 1 (water intrusion test), wherein A denotes a measurement instrument (Sartocheck 4 from Sartorius Stedim Biotech GmbH) and C denotes a structure comprising a pleated filter cartridge having two end caps and filter housing B.

Various filter units according to the present invention and according to the prior art (pleated filter cartridge having two end caps and filter housing B, specifically a filter capsule, the structure of which is shown in FIG. 5) were tested in accordance with the following test descriptions. The results obtained were the WIT value, as a measure of the integrity of the filter unit against water, and the BCT value (BCT="bacterial challenge test"), as a measure of the suitability of the filter unit for sterile-filtration.

Water Intrusion Test (WIT) Conditions

The upstream side of the filter housing is filled with water. This is followed by application of 1.5 bar of pressure to the system and stabilization for 10 min. During the test time of 10 min, the water intrudes into the first layer of the membrane. The drop in pressure is measured. From the measured volume of the water which is required in order to compensate for the drop in pressure, and from the drop in pressure and also the known test time, the WIT value is calculated as a measure of the water intrusion. The test is carried out with the aid of a Sartocheck 4 measurement instrument from Sartorius Stedim Biotech GmbH.

Bacterial Challenge Test (BCT) Conditions

The BCT is carried out in accordance with ASTM F838-15. The microbe used is *Brevundimonas diminuta*. A result of CFU=0 is rated as "sterile".

In the following examples and comparative examples, the following porous separation plies B were used.

TABLE 2

|  | Mean nonwoven thickness [μm] | Grammage [g/m$^2$] |
| --- | --- | --- |
| PET 1 | 250 | 45 |
| PET 2 | 250 | 35 |
| PET 3 | 150 | 25 |
| PET 4 | 230 | 30 |
| PET 5 | 110 | 30 |
| PP/PE | 450 | 90 |

The hydrophobically modified membrane used was a membrane as described in DE 10 2011 121 018 A1.

The results of the measurements carried out are specified in Tables 3 to 7 below. If the filter units were irradiated before the particular test, this is specified together with the radiation dose.

Example 1

The tested filter cartridge, used as capsule, exhibited the ply sequence BAB (PP/PE core-sheath nonwoven//hydrophobically modified membrane//PP/PE core-sheath nonwoven). Individual items (indicated by numbers (No.)) of structurally identical batches in each case were tested.

The filter capsules of build heights 7, 9 and 10, as specified in the following tables, respectively exhibited a filter area of about 0.06 m$^2$, 0.17 m$^2$ and 0.55 m$^2$.

TABLE 3

| Ply sequence | Build height | Batch | No. | Microbial count [CFU] | Treatment |
|---|---|---|---|---|---|
| BAB | 9 | 121 | 2 | 0 | Irradiated, 50 kGy |
|  |  |  | 28 | 0 |  |
|  |  | 120 | 1 | 0 |  |
|  |  |  | 2 | 0 |  |
|  |  | 119 | 14 | 0 |  |
|  |  |  | 18 | 0 |  |
| BAB | 10 | 141 | 99 | 0 |  |
|  |  |  | 108 | 0 |  |

All the tested filter capsules of batches 119, 120, 121 and 141 were sterile (CFU=0).

TABLE 4

| Ply sequence | Build height | Batch | No. | WIT value [ml/10 min] | Treatment |
|---|---|---|---|---|---|
| BAB | 9 | 121 | 1 | 0.8 | Irradiated, 50 kGy |
|  |  |  | 21 | 0.8 |  |
|  |  |  | 38 | 0.8 |  |
|  |  | 120 | 6 | 1.2 |  |
|  |  |  | 25 | 1.4 |  |
|  |  |  | 38 | 0.9 |  |
| BAB | 10 | 141 | 107 | 2.4 |  |
|  |  |  | 115 | 2.3 |  |
|  |  |  | 93 | 2.5 |  |

The combination of two PP/PE core-sheath nonwovens with a hydrophobically modified membrane in the ply sequence BAB is, after irradiation, WIT-testable and also capable of sterile-filtration as per BCT in accordance with ASTM F838-15.

Comparative Example 1

The tested filter cartridges, used in capsules, exhibited the ply sequences PET1//hydrophobically modified membrane//PET1 or PET1//PET2//hydrophobically modified membrane//PET2//PET1.

TABLE 5

| Ply sequence | Build height | Batch | No. | Microbial count [CFU] | Treatment |
|---|---|---|---|---|---|
| PET1//PET2//hydrophob. mod. membrane//PET2//PET1 | 9 | 98 | 54 | Film | Irradiated, 50 kGy |
|  |  |  | 65 | 362 |  |
|  |  | 24 | 37 | Lawn |  |
|  |  | 23 | 12 | Lawn |  |
|  |  |  | 21 | Lawn |  |
|  |  | 177 | 8 | Film |  |
|  |  |  | 16 | Film |  |
| PET1//hydrophob. mod. membrane//PET1 | 7 | 458 | 12 | Film |  |
|  | 9 | 468 | 4 | Lawn |  |

The designations "Film" or "Lawn" indicate a microbial infestation which can already be identified with the naked eye.

TABLE 6

| Combination | Build height | Batch | No. | WIT [ml/10 min] | Treatment |
|---|---|---|---|---|---|
| PET1//PET2//hydrophob. mod. membrane//PET1 | 9 | 177 | 9 | 15.7 | Irradiated, 50 kGy |
|  |  |  | 12 | 19.9 |  |
|  |  |  | 14 | 27.2 |  |
|  |  |  | 18 | 15.8 |  |
| PET1//PET2//hydrophob. mod. membrane//PET2//PET1 | 9 | 411 | 25 | 31.2 |  |
| PET1//hydrophob. mod. membrane//PET1 | 9 | 456 | 20 | 20.9 |  |
|  |  | 115 | 9 | 82.1 |  |
|  |  | 113 | 1 | 78 |  |
|  |  |  | 5 | 94 |  |
|  |  | 466 | 1 | 14.5 |  |
|  |  |  | 2 | 20.2 |  |
|  |  |  | 15 | 104.3 |  |

The tested combinations of polyester nonwoven with hydrophobically modified membrane are, after irradiation, neither WIT-testable (very high WIT results) nor capable of sterile-filtration as per BCT.

Example 2

In this example, further filter cartridges according to the present invention, used as capsule, and comparative filter cartridges with various PET combinations as porous separation ply B were tested. The results are summarized in Table 7 below.

TABLE 7

| Ply sequence | Build height | Batch | Proportion (%) of filter cartridges tested as sterile; number of cartridges tested in parentheses | Treatment |
|---|---|---|---|---|
| PET1//PET2//hydrophob. mod. membrane//PET2//PET1 | 9 | 200 | 70% (10) | Untreated |
| PET1//PET4//hydrophob. mod. membrane//PET4//PET1 |  | 207 | 30% (10) |  |
| PET1//PET5//hydrophob. mod. membrane//PET5//PET1 |  | 208 | 50% (10) |  |
| PET1//hydrophob. mod. membrane//PET1 |  | 239 | 0% (2) |  |
| PET1//PET3//hydrophob. mod. membrane//PET3//PET1 |  | 245 | 30% (10) |  |
| PET1//PET1//hydrophob. mod. membrane//PET1//PET1 |  | 254 | 20% (5) |  |
| PP/PE//hydrophob. mod. membrane//PP/PE | 9 | 119 | 100% (10) | Irradiated, 50 kGy |
|  |  | 120 | 100% (10) |  |
|  |  | 121 | 100% (10) |  |

As is evident from Table 7, the comparative filter cartridges are not capable of sterile-filtration as per BCT, even without gamma-irradiation. In contrast, the filter units according to the invention remain capable of sterile-filtration as per BCT, even after gamma-irradiation.

The present invention provides porous sheet products which make it possible to produce improved filter units. Since the sheath material of the polyolefin core-sheath nonwoven melts at a low temperature, the sheet product according to the invention can be pleated and embedded into an anchoring material at low temperatures. If a hydrophobically modified membrane is used as porous membrane ply A, the hydrophobic modification is protected from decomposition due to high processing temperatures. (Decomposition of hydrophobization may lead to the formation of hydrophilic regions, the result being that the properties of the filter may change greatly, and this could result in the impairment of the function of the filter element, especially as air filter. Especially the air-flow capacity and the WIT test behavior could deteriorate.) The sheet products and filter elements according to the invention are both WIT-testable and capable of sterile-filtration as per BCT even after gamma-irradiation, this not being the case for comparable filter elements according to the prior art. Moreover, particularly stable pleatings can be generated in a gentle manner from the sheet products according to the invention.

The invention claimed is:

1. A filter element comprising:
   a porous sheet product having at least one of the following ply A and at least two of the following ply B:
   A: a porous membrane; and
   B: a porous separation ply constructed from polyolefin core-sheath fibers, the sheath material having a lower melting temperature than the core material;
   the porous sheet product exhibiting a radiation resistance of at least 20 kGy, wherein the plies A and B lie on top of one another in a loose manner without being firmly connected to one another and the two external plies of the sheet product are formed by one ply B in each case, and
   at least one anchoring element, and
   edge regions of the porous membrane A being embedded into the anchoring element in a fluid-tight manner.

2. The filter element as claimed in claim 1,
   wherein the core material of the porous separation ply B is polypropylene and the sheath material of the porous separation ply B is polyethylene.

3. The filter element as claimed in claim 1, wherein the porous membrane A is hydrophobic.

4. The filter element as claimed in claim 1,
   wherein the porous membrane is constructed from a polymer selected from the group consisting of polyethersulfone, polyvinylidene fluoride, a polyolefin, and mixtures thereof.

5. The filter element as claimed in claim 1, which consists of the ply sequence BAB or BAAB.

6. The filter element as claimed in claim 1, which is an air filter.

7. A method for producing the filter element of claim 1, comprising:
   (I) providing a porous sheet product; having at least one of the following ply A and at least two of the following ply B:
   A: a porous membrane; and
   B: a porous separation ply constructed from polyolefin core-sheath fibers, the sheath material having a lower melting temperature than the core material;
   the porous sheet product exhibiting a radiation resistance of at least 20 kGy, wherein the plies A and B lie on top of one another in a loose manner without being firmly connected to one another and the two external plies of the sheet product are formed by one ply B in each case;
   (II) providing the at least one anchoring element; and
   (Ill) embedding the edge regions of the porous membrane A into the at least one anchoring element in a fluid-tight manner.

8. The use of the filter element of claim 1 for sterile-filtration comprising a step of sterile filtering.

* * * * *